United States Patent [19]

Merger et al.

[11] 4,336,403

[45] Jun. 22, 1982

[54] PREPARATION OF METHYL METHACRYLATE BY REACTION OF METHYL PROPIONATE AND METHANOL

[75] Inventors: Franz Merger, Frankenthal; Gerd Fouquet, Neustadt, both of Fed. Rep. of Germany

[73] Assignee: BASF Aktiengesellschaft, Fed. Rep. of Germany

[21] Appl. No.: 228,284

[22] Filed: Jan. 26, 1981

[30] Foreign Application Priority Data

Feb. 7, 1980 [DE] Fed. Rep. of Germany ....... 3004467

[51] Int. Cl.$^3$ ............................................ C07C 67/343
[52] U.S. Cl. .................................... 560/211; 252/439
[58] Field of Search ................. 560/211, 210; 568/472

[56] References Cited

U.S. PATENT DOCUMENTS 3,014,958 12/1981 Koch et al. .
3,654,345 4/1972 Jentsch ................................. 560/210
4,014,939 3/1977 Osugi et al. .
4,054,609 10/1977 Osugi et al. .

FOREIGN PATENT DOCUMENTS 1207415 9/1970 United Kingdom .
1224736 3/1971 United Kingdom .
1428277 3/1976 United Kingdom .
1447669 8/1976 United Kingdom .

*Primary Examiner*—Natalie Trousof
*Assistant Examiner*—L. Hendriksen
*Attorney, Agent, or Firm*—Keil & Witherspoon

[57] ABSTRACT

Methyl methacrylate is prepared by reacting methyl propionate and methanol at 200°–550° C. over a catalyst mixture which has a condensing action and is capable of dehydrogenating methanol to formaldehyde.

2 Claims, No Drawings

PREPARATION OF METHYL METHACRYLATE BY REACTION OF METHYL PROPIONATE AND METHANOL

U.S. Pat. No. 3,014,958 discloses the reaction of aqueous formaldehyde with methyl propionate, in the molar ratio of from 1:1.5 to 1:20, at 225°–450° C., in the presence of a dehydration catalyst. The reaction is carried out in the presence of not less than 7% by weight of methyl methacrylate, and with addition of methanol. If a catalyst of the general formula $K_2O.MgO.Fe_2O_3$ is employed, a yield of methyl methacrylate of 84%, based on formaldehyde, is achieved, if a molar ratio of methyl propionate:formaldehyde:water:methyl methacrylate of 10:1:1:0.8 is employed and small amounts of methanol are present. If calcium phosphate, calcium sulfate, aluminum phosphate or magnesium phosphate is used as the catalyst, the yields obtained are lower.

British Pat. No. 1,447,669 discloses the preparation of $\alpha,\beta$-ethylenically unsaturated acids or their esters by reacting formaldehyde with the corresponding alkanoic acid or its esters in the presence of a catalyst comprising pyrogenic silica, which may be mixed with up to 10%, of its weight, of pyrogenic zirconium dioxide and has a total surface area of 150–300 $m^2/g$, a porosity of 3–15 $cm^3/g$ and a pore size distribution which is such that not less than 50% of the pores have a diameter greater than 10,000 Å and fewer than 30% of the pores have a diameter less than 1,000 Å. The catalyst used is activated with a basic compound and then calcined. The reaction is carried out at 330°–390° C., the molar ratio of alkanoic acid, or alkanoic acid esters, to formaldehyde being from 0.3:1 to 3.0:1. The preferred basic activators include sodium hydroxide, potassium hydroxide, cesium hyroxide, calcium hydroxide and calcium carbonate. In this patent, the only Example which relates to the reaction of methyl propionate employs a molar ratio of methyl propionate:formaldehyde:water:methanol of 20:20:59:1, at 370° C., and gives 25% conversion, a mixture of methacrylic acid and methyl methacrylate being produced in a combined yield of 63% or 44%, based on formaldehyde or methyl propionate respectively. A disadvantage of the process is that 40% of the methyl propionate employed undergoes hydrolysis to propionic acid.

British Pat. No. 1,428,277 discloses the preparation of methyl methacrylate from methyl propionate, formaldehyde and water, in the presence or absence of methanol and in the presence of compounds of the first main group of the periodic table, at a reaction temperature of 400°–600° C. The catalysts used have a specific surface area of 350–1,000 $m^2/g$ and the molar ratio of water:formaldehyde is from 0.01:1 to 10:1. In Example 1, employing a molar ratio of methyl propionate:formaldehyde:water:methanol of 4.5:1:5.3:6.7, a formaldehyde conversion of 67% and a methyl methacrylate yield of 92%, based on formaldehyde, are obtained. The catalyst used is silica gel which has a specific surface area of 600 $m^2/g$ and has been calcined at 500° C. and activated with KOH. Hydrolysis of the methyl propionate to propionic acid is not described in this patent. However, unless water is added, the process gives virtually no condensation to methyl methacrylate (cf. Example 4, run 3).

German Laid-Open Application DOS No. 2,525,174 discloses the dehydrogenation of methanol at 500°–750° C. in the presence of copper, zinc and sulfur as catalyst components. A methanolic formaldehyde solution, containing 30–85% by weight of formaldehyde, is obtained.

German Laid-Open Application DOS No. 2,627,421 discloses the dehydrogenation of methanol at 500°–750° C. in the presence of a catalyst which contains copper, zinc and selenium as components. The methanol conversion is up to 78% and the selectivity in respect of formaldehyde formation is up to 90%.

We have found that methyl methacrylate can be prepared by reaction of methyl propionate and methanol, at 200°–550° C., over a catalyst mixture which has a condensing action and is capable of dehydrogenating methanol. Suitable condensing catalysts are described, for example, in British Pat. Nos. 1,447,669 and 1,428,277 and in U.S. Pat. No. 3,014,958. Examples include the phosphates, silicates and oxides of aluminum in particular, but also of magnesium, calcium, titanium and zirconium, all of which compounds may or may not be modified with oxides and/or hydroxides of alkali metals and/or alkaline earth metals, especially with KOH, NaOH or CsOH, but also with CaO, $Ca(OH)_2$, MgO or $Mg(OH)_2$. Catalysts based on silicon dioxide and modified with an alkali metal oxide, especially $K_2O$, $Na_2O$ or $Cs_2O$, are of particular interest. They can advantageously be prepared from highly disperse silica obtained by flame hydrolysis of volatile silicon compounds and having a total surface area of 100–400 $m^2/g$. The modifier can be applied for impregnation.

In the novel process, the dehydrogenating and condensing catalysts employed in the reaction mixture are catalysts which permit the dehydrogenation of methanol at 200°–550° C., whilst not significantly catalyzing, under the same conditions, the hydrogenation of the methyl methacrylate formed. The catalysts in general function without addition of gaseous oxygen to the reaction mixture, but small traces of oxygen, such as may be introduced as an impurity in the starting materials, in general do not interfere. The dehydrogenation catalysts preferably contain copper and zinc as well as tellurium and/or selenium and/or sulfur, if appropriate in the form of the oxides. Oxide catalysts which can contain copper, zinc and tellurium, have proved particularly appropriate. In the especially suitable condensing and dehydrogenating catalysts, the atomic ratio of copper:zinc:tellurium and/or selenium is in general 1:0.01–0.5:0.001–0.3, preferably 1:0.05–0.4:0.005–0.2. Such catalysts can be prepared, for example, by kneading copper oxide with zinc oxide and tellurium dioxide (and/or selenium dioxide and/or ammonium sulfate) in the presence of water, drying the mixture at 130° C. and then pressing it to form pills, with or without admixture of a carrier. It is also possible to mix the preferred condensing catalyst constituent, especially alkali-activated silicon dioxide, with the oxide constituents of the preferred dehydrogenating catalyst, with addition of a small amount of water, and to dry the mixture and press it to form pills. In the oxide catalyst of the type mentioned, the copper oxide is completely or partially reduced to metallic copper, during use, by the hydrogen formed on dehydrogenation of methanol. In some cases it is advantageous to reduce the catalyst prior to use, for example with gaseous hydrogen, at 200°–600° C.

The process may be carried out with the catalysts in the form of a fixed bed in the reaction vessel, for example a tubular reactor. However, a fluidized bed can also be used. The reaction temperature is in general 200°–550° C., preferably 250°–500° C. The molar ratio of methyl propionate to methanol is mostly from 10:1 to 1:10, preferably from 5:1 to 1:5. Water may be present during the process but is not essential. The space velocity (amount of educt per unit of catalyst per hour) is mostly from 10 to 0.05, preferably from 5 to 0.05.

The reaction mixture can be worked up in a conventional manner and unconverted starting material can be recycled to the reaction.

The statement that the catalysts according to the invention are capable of dehydrogenating methanol to formaldehyde is not to be taken to imply that the process according to the invention (dehydrogenation and condensation) actually proceeds via such a reaction.

It is surprising that the dehydrogenation of methanol and the reaction of the formaldehyde, believed to be formed as an intermediate, with methyl propionate to give methyl methacrylate can be carried out in a one-vessel process, since it was not to be expected that the hydrogen liberated during the dehydrogenation of the methanol would not cause substantial hydrogenation of the methyl methacrylate in the presence of a catalyst, nor was it to be expected that the methyl methacrylate would not interfere with the dehydrogenation of the methanol. The preferred dehydrogenating catalysts containing copper, zinc and tellurium are furthermore novel. These catalysts are particularly suitable since, surprisingly, they do not lose any tellurium during the reaction, whilst the conventional catalysts containing copper, zinc and sulfur or selenium undergo depletion in sulfur or selenium during the reaction.

It is an advantage of the novel process that it permits particularly simple and economical preparation of methyl methacrylate from methyl propionate.

Each of the Examples described below is carried out as follows:

A solution of methyl propionate in methanol is vaporized in a quartz tube, of 20 cm length and 3 cm internal diameter, which is filled with Raschig rings, and the gaseous reactants are then passed into the catalyst-filled reactor. The latter consists of a quartz tube which has an internal diameter of 3 cm and can be heated over a length of 30 cm. The reaction mixture leaving the reactor is examined by gas chromatography. The selectivities recorded in the Examples below were calculated from the following equations:

$$\text{Conversion (\%)} = \frac{\text{moles of methyl propionate converted}}{\text{moles of methyl propionate introduced}} \times 100$$

$$\text{Selectivity (\%)} = \frac{\text{moles of methyl methacrylate formed}}{\text{moles of methyl propionate converted}} \times 100$$

EXAMPLE 1

(a) Preparation of the Catalyst 85.8 g of copper(II) oxide, 10 g of zinc oxide and 4.2 g of tellurium dioxide are mixed with 50 g of water and the mixture is dried at 130° C. The dried oxide mixture is pressed to form pills, which are 3 mm thick and have a diameter of 3 mm.

(b) 100 g of highly disperse silica (HDK-N-20 from Wacker) are suspended in 1,000 cm³ of an 0.1% strength aqueous potassium hydroxide solution. The water is then evaporated off in a rotary evaporator and the residue is dried for 2 hours at 130° C. The dried, KOH-activated SiO$_2$ is pressed to form pills which are 3 mm thick and have a diameter of 3 mm, and these are then calcined for 4 hours at 450° C.

(c) Reaction 30 cm³ (=65.1 g) of the catalyst from (a) and 150 cm³ (=87.3 g) of the catalyst from (b) are introduced in layers, starting with 10 cm³ of the former and 50 cm³ of the latter, into the reactor. The filled reactor is then heated to 420° C. and, per hour, a mixture of 7.7 g of methyl propionate and 13.9 g of methanol is passed over the catalyst. The methyl propionate is converted to methyl methacrylate with a selectivity of 81.4%. The conversion is 13.2%. Methyl isobutyrate is formed with a selectivity of 4.9%.

EXAMPLE 2

The procedure described in Example 1c) is followed, but, per hour, a mixture of 89 g of methyl propionate and 80.8 g of methanol is passed through the reactor. The methyl propionate is converted to methyl methacrylate with a selectivity of 76%, whilst methyl isobutyrate is formed with a selectivity of 3.4%.

EXAMPLE 3

(a) Preparation of the catalyst 78.1 g of copper(II) oxide, 10.9 g of zinc oxide and 10.9 g of selenium dioxide are kneaded with 50 g of water and the mixture is dried at 130° C. The dried mixture is pressed to form 3 mm×3 mm pills.

(b) Reaction 60 ml (=137 g) of the catalyst are introduced into the reactor and, per hour, a mixture of 17.6 g of methyl propionate and 32 g of methanol is passed over the catalyst, at 450° C. The methyl propionate is converted to methyl methacrylate with a selectivity of 46.1%. The conversion is 5%. Methyl isobutyrate is formed with a selectivity of 9.3%.

EXAMPLE 4

(a) Preparation of the catalyst 85.8 g of copper(II) oxide, 10 g of zinc oxide and 4.2 g of tellurium dioxide are kneaded with 50 g of water and the mixture is dried at 130° C. and then pressed to form 3 mm×3 mm pills.

(b) 100 g of highly disperse silica (HDK-N-20 from Wacker) are suspended in 1,000 cm³ of 0.1% strength aqueous potassium hydroxide solution and the water is then distilled from the suspension in a rotary evaporator. The residue is dried for 2 hours at 130° C., heated for 4 hours at 450° C. and finally crushed to form granules of 2–3 mm particle size. The bulk density of the catalyst is 0.3 g/cm³.

(c) Reaction 30 cm³ (=65 g) of catalyst (a) and 150 cm³ (=45.9 g) of catalyst (b) are arranged in the reactor as described in Example 1. The catalyst is then heated to 420° C. and, per hour, a mixture of 55.3 g of methyl propionate and 20.1 g of methanol is passed through the reactor. The conversion of methyl propionate is 5.8%, methyl methacrylate being formed with a selectivity of 85.6%. Methyl isobutyrate is obtained with a selectivity of 4.3%.

EXAMPLE 5

The procedure described in Example 4(c) is followed, but, per hour, 18.3 g of methanol and 20.1 g of methyl propionate are passed through the reactor. The conversion of methyl propionate is 14.6% and the selectivity is 76.0%. Methyl isobutyrate is obtained with a selectivity of 7.3%.

EXAMPLE 6

30 cm³ (=65 g) of catalyst (a) from Example 4 and 145 cm³ (=45.9 g) of catalyst (b) from Example 4 are mixed and introduced into the reactor. The catalyst is heated to 420° C. and, per hour, a mixture of 8.5 g of methanol and 9.4 g of methyl propionate is passed through the reactor. The conversion of methyl propionate is 14%, methyl methacrylate being formed with a selectivity of 78.3%. Methyl isobutyrate is formed with a selectivity of 5.9%.

EXAMPLE 7

8 cm³ (=18.3 g) of catalyst pills from Example 3(a) and 45 cm³ of the catalyst described in Example 1(b) are mixed and introduced into the reactor. The catalyst is heated to 420° C. and, per hour, a mixture of 7.5 g of methyl propionate and 8.3 g of methanol is passed through the reactor. 14.4% of methyl propionate is converted, methyl methacrylate being obtained with a selectivity of 49.8%. Methyl isobutyrate is obtained with a selectivity of 8.7%.

EXAMPLE 8

30 cm³ (=65 g) of the catalyst (a) of Example 4 and 150 cm³ (=98.5 g) of 3 mm tablets of aluminum oxide are mixed and the mixture is introduced into the reactor and heated to 400° C. Per hour, a mixture of 26.8 g of methyl propionate and 24.3 g of methanol is passed through the reactor. The conversion of methyl propionate is 11.0%, methyl methacrylate being formed with a selectivity of 8.2%. Methyl isobutyrate is obtained with a selectivity of 6.4%.

EXAMPLE 9

30 cm³ (=65 g) of catalyst (a) from Example 4 and 150 cm³ (=98.5 g) of 1.5 mm extrudates of titanium dioxide are mixed, filled into the reactor, and heated to 410° C. Per hour, a mixture of 24.1 g of methyl propionate and 23.2 g of methanol is passed through the reactor. The conversion of methyl propionate is 13.6%, methyl methacrylate being formed with a selectivity of 50.1%. Methyl isobutyrate is obtained with a selectivity of 3.5%.

EXAMPLE 10

30 cm³ (=65 g) of catalyst (a) from Example 4 and 150 cm³ (=117.5 g) of 3 mm extrudates of magnesium oxide are arranged in the reactor as described in Example 1. The catalyst is heated to 350° C. and, per hour, a mixture of 26.8 g of methyl propionate and 24.3 g of methanol is passed through the reactor. The conversion of methyl propionate is 6.3%, methyl methacrylate being formed with a selectivity of 8.2%. Methyl isobutyrate is obtained with a selectivity of 16.2%.

EXAMPLE 11

30 cm³ (=65 g) of catalyst (a) from Example 4 and 150 ml (=73.6 g) of 1.5 mm extrudates of aluminum phosphate, modified with 5.9% of potassium (which is kneaded into the mixture as potassium propionate) are arranged in the reactor as described in Example 1. The catalyst is heated to 300° C. and, per hour, 20.1 g of methyl propionate and 18.3 g of methanol are passed through the reactor. The conversion of methyl propionate is 17%, methyl methacrylate being formed with a selectivity of 14.1%. Methyl isobutyrate is obtained with a selectivity of 7.6%.

We claim:

1. A process for the preparation of methyl methacrylate from methyl propionate and methanol at 200°–550° C. in the presence of a catalyst, wherein the reaction is carried out over a catalyst mixture consisting of an oxide catalyst containing copper, zinc and tellurium in the atomic ratio of 1:0.01–0.5:0.001–0.3 and of silicon dioxide modified with potassium.

2. A process as claimed in claim 1 in which the molar ratio of methyl propionate to methanol is from 10:1 to 1:10.

* * * * *